(12) United States Patent
Blanton et al.

(10) Patent No.: US 7,579,396 B2
(45) Date of Patent: Aug. 25, 2009

(54) POLYMER COMPOSITE

(75) Inventors: Thomas N. Blanton, Rochester, NY (US); Narasimharao Dontula, Rochester, NY (US); Seshadri Jagannathan, Rochester, NY (US); Kevin L. Bishop, Rochester, NY (US); David W. Sandford, Rochester, NY (US); Craig L. Barnes, LeRoy, NY (US)

(73) Assignee: Eastman Kodak Company, Rochester, NY (US)

( * ) Notice: Subject to any disclaimer, the term of this patent is extended or adjusted under 35 U.S.C. 154(b) by 64 days.

(21) Appl. No.: 11/669,830

(22) Filed: Jan. 31, 2007

(65) Prior Publication Data

US 2008/0181969 A1    Jul. 31, 2008

(51) Int. Cl.
C08K 3/10       (2006.01)
C08K 5/13       (2006.01)
C08K 5/105      (2006.01)
C08K 5/372      (2006.01)

(52) U.S. Cl. .................... 524/403; 524/81; 524/291; 524/423

(58) Field of Classification Search .............. 524/81, 524/291, 423, 403
See application file for complete search history.

(56) References Cited

U.S. PATENT DOCUMENTS

| | | |
|---|---|---|
| 2,230,371 A | 2/1941 | Bolton |
| 4,024,103 A | 5/1977 | Heinrich et al. |
| 4,525,410 A | 6/1985 | Hagiwara et al. |
| 4,938,955 A | 7/1990 | Niira et al. |
| 5,064,599 A | 11/1991 | Ando et al. |
| 5,180,402 A | 1/1993 | Kubota et al. |
| 5,405,644 A | 4/1995 | Ohsumi et al. |
| 5,880,044 A | 3/1999 | Shimiz |
| 5,888,526 A | 3/1999 | Tsubai et al. |
| 6,015,854 A | 1/2000 | McCullough, Jr. |
| 6,022,946 A | 2/2000 | McCullough, Jr. |
| 6,187,456 B1 | 2/2001 | Lever |
| 6,197,886 B1 | 3/2001 | Chatterjee et al. |
| 6,274,519 B1 | 8/2001 | Omori et al. |
| 6,436,420 B1 | 8/2002 | Antelman |
| 6,468,521 B1 | 10/2002 | Pedersen et al. |
| 6,479,144 B2 | 11/2002 | Petrea et al. |
| 6,538,056 B1 | 3/2003 | Webster |
| 6,585,843 B2 | 7/2003 | Nickell et al. |
| 6,585,989 B2 | 7/2003 | Herbst et al. |
| 6,716,895 B1 | 4/2004 | Terry |
| 6,726,791 B1 | 4/2004 | Oelund et al. |
| 6,770,693 B2 | 8/2004 | Stein et al. |
| 6,774,170 B2 | 8/2004 | Webster |
| 6,881,744 B2 | 4/2005 | Redkar et al. |
| 7,041,723 B2 | 5/2006 | Kimura |
| 2001/0034419 A1* | 10/2001 | Kanayama et al. .......... 525/439 |
| 2003/0225356 A1* | 12/2003 | Kulichikhin et al. .......... 602/54 |
| 2005/0131100 A1 | 6/2005 | Herbst et al. |

FOREIGN PATENT DOCUMENTS

| | | |
|---|---|---|
| BE | 617194 | 5/1962 |
| DE | 1210855 | 2/1966 |
| EP | 1 190 622 | 3/2002 |
| JP | 62-270642 | 11/1987 |
| JP | 03-271208 | 12/1991 |
| JP | 04-114038 | 4/1992 |
| JP | 7-233279 | 9/1995 |
| JP | 8-026921 | 1/1996 |
| JP | 10-120833 | 5/1998 |
| JP | 28-41115 B2 | 12/1998 |
| WO | WO 2004/033545 | 4/2004 |

OTHER PUBLICATIONS

J.A. Howard; "Autoxidation And Antioxidants, Basic Principles And New Developments"; Rubber Chemistry And Technology; 1974; pp. 988-989.
A. Goetz et al; "The Oligodynamic Effect Of Silver"; Silver In Industry; 1940; pp. 401-429.
I.B. Roamns; "Oligodynamic Metals"; Disinfection, Sterilization And Preservation; 1968; pp. 372-400.
Stewart C. Harvey; "Antiseptics And Disinfectants; Fungicides; Ectoparasiticides" The Pharmacological Basis Of Therapeutics; pp. 964-987, (1980).
Stewart C. Harvey; "Heavy Metals" The Pharmacological Basis Of Therapeutics; pp. 924-945, (1975).

* cited by examiner

*Primary Examiner*—Kriellion A Sanders
(74) *Attorney, Agent, or Firm*—J. Lanny Tucker

(57) ABSTRACT

A polymer composite comprising a thermoplastic polymer compounded with a phenolic antioxidant, an organo-disulfide antioxidant, and a silver-based antimicrobial agent. The specified combination of antioxidant stabilizers is superior in inhibiting undesirable discoloration of thermoplastic polymers in the presence of compounded silver-based antimicrobial agents. A process of preparing such a composite, comprising compounding the phenolic antioxidant and organo-disulfide antioxidant with the thermoplastic polymer prior to compounding the silver-based antimicrobial agent with the thermoplastic polymer.

19 Claims, No Drawings

POLYMER COMPOSITE

FIELD OF THE INVENTION

The present invention relates to improvements in color of melt-processed thermoplastic polymer composites and plastic objects made there of, within which a silver-based antimicrobial agent has been introduced. More particularly, the invention is directed towards use of a specified combination of antioxidant stabilizers in such polymer composites, and an improved method of introducing the combination of antioxidant stabilizers and silver-based antimicrobial agents to a thermoplastic polymer.

BACKGROUND OF THE INVENTION

Widespread attention has been focused in recent years on the consequences of bacterial contamination contracted by food consumption or contact with common surfaces and objects. Some noteworthy examples include the sometimes fatal outcome from food poisoning due to the presence of particular strains of *Eschericia coli* in undercooked beef; *Salmonella* contamination in undercooked and unwashed poultry food products; as well as illnesses and skin irritations due to *Staphylococcus aureus* and other micro-organisms. Anthrax is an acute infectious disease caused by the spore-forming bacterium *bacillus anthracis*. Allergic reactions to molds and yeasts are a major concern to many consumers and insurance companies alike. Respiratory infections due to viruses such as SARS (severe acute respiratory syndrome) coronavirus, and the return of the H5N1 virus and mutations thereof, now commonly referred to as the avian flu or bird flu, which was responsible for the great pandemic influenza of 1918, have become major public health issues. In addition, significant fear has arisen in regard to the development antibiotic-resistant strains of bacteria, such as methicillin-resistant *Staphylococcus aureus* (MRSA) and vancomycin-resistant *Enterococcus* (VRE). The Centers for Disease Control and Prevention estimates that 10% of patients contract additional diseases during their hospital stay and that the total deaths resulting from these nosocomially-contracted illnesses exceeds those suffered from vehicular traffic accidents and homicides. In response to these concerns, manufacturers have begun incorporating antimicrobial agents into materials used to produce objects for commercial, institutional and residential use.

The antimicrobial properties of silver have been known for several thousand years. The general pharmacological properties of silver are summarized in "Heavy Metals" and "Antiseptics and Disinfectants: Fungicides; Ectoparasiticides"— by Stewart C. Harvey in *The Pharmacological Basis of Therapeutics*, Fifth Edition, by Louis S. Goodman and Alfred Gilman (editors), published by MacMillan Publishing Company, NY, 1975. It is now understood that the affinity of silver ion for biologically important moieties such as sulfhydryl, amino, imidazole, carboxyl and phosphate groups are primarily responsible for its antimicrobial activity.

The attachment of silver ions to one of these reactive groups on a protein results in the precipitation and denaturation of the protein. The extent of the reaction is related to the concentration of silver ions. The diffusion of silver ion into mammalian tissues is self-regulated by its intrinsic preference for binding to proteins through the various biologically important moieties on the proteins, as well as precipitation by the chloride ions in the environment. Thus, the very affinity of silver ion to a large number of biologically important chemical moieties (an affinity which is responsible for its action as a germicidal/biocidal/viricidal/fungicidal/bacteriocidal agent) is also responsible for limiting its systemic action— silver is not easily absorbed by the body. This is a primary reason for the tremendous interest in the use of silver containing species as an antimicrobial i.e. an agent capable of destroying or inhibiting the growth of microorganisms, including bacteria, yeast, fungi and algae, as well as viruses.

In addition to the affinity of silver ions for biologically relevant species, which leads to the denaturation and precipitation of proteins, some silver compounds, those having low ionization or dissolution ability, also function effectively as antiseptics. Distilled water in contact with metallic silver becomes antibacterial even though the dissolved concentration of silver ions is less than 100 ppb. There are numerous mechanistic pathways by which this oligodynamic effect is manifested i.e. by which silver ion interferes with the basic metabolic activities of bacteria at the cellular level, thus leading to a bacteriocidal and/or bacteriostatic effect.

A detailed review of the oligodynamic effect of silver can be found in "Oligodynamic Metals" by I. B. Romans in *Disinfection Sterilization and Preservation*, C. A. Lawrence and S. S. Bloek (editors), published by Lea and Fibiger (1968) and "The Oligodynamic Effect of Silver" by A. Goetz, R. L. Tracy and F. S. Harris, Jr. in *Silver in Industry*, Lawrence Addicks (editor), published by Reinhold Publishing Corporation, 1940. These reviews describe results that demonstrate that silver is effective as an antimicrobial agent towards a wide range of bacteria.

While it is well known that silver-based agents provide excellent antimicrobial properties, aesthetic problems due to discoloration are frequently a concern. This is believed to be due to several root causes, including the inherent thermal and photo-instability of silver ions, along with other mechanisms. A wide range of silver salts are known to be thermally and photolytically unstable, discoloring to form brown, gray or black products. Silver ion may be formally reduced to its metallic state, assuming various physical forms and shapes (particles and filaments), often appearing brown, gray or black in color. Reduced forms of silver that form particles of sizes on the order of the wavelength of visible light may also appear to be pink, orange, yellow, beige and the like due to light scattering effects. Alternatively, silver ion may be formally oxidized to silver peroxide, a gray-black material. In addition, silver ion may simply complex with environmental agents (e.g. polymer additives, catalyst residues, impurities, surface coatings, etc.) to form colored species without undergoing a formal redox process. Silver ion may attach to various groups on proteins present in human skin, resulting in the potentially permanent dark stain condition known as argyria. Silver ion may react with sulfur to form silver sulfide, for which two natural mineral forms, acanthite and argentite, are known to be black in color. Pure silver sulfate (white in color) has been observed to decompose by light to a violet color.

In any given practical situation, a number of mechanisms or root causes may be at work in generating silver-based discoloration, complicating the task of providing a solution to the problem. For example, Coloplast, as describe in U.S. Pat. No. 6,468,521 and U.S. Pat. No. 6,726,791, disclose the development of a stabilized wound dressing having antibacterial, antiviral and/or antifungal activity characterized in that it comprises silver complexed with a specific amine and is associated with one or more hydrophilic polymers, such that it is stable during radiation sterilization and retains the activity without giving rise to darkening or discoloration of the dressing during storage. Registered as CONTREET®, the dressing product comprises a silver compound complexed specifically with either ethylamine or tri-hydroxymethylaminomethane. These specific silver compounds, when used in conjunction with the specific polymer binders carboxymethylcellulose or porcine collagen, are said to have improved resistance to discoloration when exposed to heat, light or radiation sterilization and contact with skin or tissue.

The point in time when discoloration of a composition associated with a silver-based additive appears can range from early in the manufacturing process to late in a finished article's useful life. For example, thermal instability can set in shortly after introduction of the silver-based additive into a high temperature melt-processed polymer, or much later during long-term storage of the material or finished article at lower (e.g. ambient) temperatures, sometimes referred to as long-term heat stability (LTHS). Likewise, photo-instability can result from short-term exposure to high-energy radiation processing or radiation sterilization, or later from long-term exposure of the material or finished article to ambient light (e.g. requiring ultraviolet (UV) stabilization). In addition, polymeric materials are well known to inherently discolor to some degree either during high temperature melt processing, or later due to aging in the presence of light, oxygen and heat. Thermoplastic polymers such as polyolefins are typically processed at temperatures between about 200-280° C. and will degrade under these conditions by an oxidative chain reaction process that is initiated by free-radical formation. Free radicals (R*) formed either along the polymer backbone or at terminal positions will react quickly with oxygen ($O_2$) to form peroxy radicals (ROO*), which in turn can react with the polymer to form hydroperoxides (ROOH) and another free radical (R*). The hydroperoxide can then split into two new free radicals, (RO*) and (*OH), which will continue to propagate the reaction to other polymer chains. It is known in the art that antioxidants and light stabilizers can prevent or at least reduce the effects of these oxidative chain reactions. Several types of additives are added to polymers to protect them during processing and to achieve the desired end-use properties. Additives are generally divided into groups: stabilizers and modifiers. Typical modifiers are antistatic-and antifogging agents, acid scavengers, blowing agents, cling agents, lubricants and resins, nucleating agents, slip- and anti-blocking agents as well as fillers, flame retardants, compatibilizers and crosslinkers. Antioxidant stabilizers are typically classified as (1) free-radical scavengers or primary antioxidants, and (2) hydroperoxide decomposers or secondary antioxidants. While not being held to any particular microscopic theory, the mechanism of antioxidants is described in "Rubber Chemistry and Technology" 47 (1974), No. 4, pages 988 and 989. The instant invention is directed primarily at reducing discoloration often seen in melt-processed thermoplastic polymers immediately following compounding, extrusion or molding at high temperature.

Primary antioxidants are added to polymers mainly to improve long-term heat stability of the final fabricated article. Primary antioxidants are often called free radical scavengers because they are capable of reacting quickly with peroxy or other available free radicals to yield an inert or much less reactive free radical species, thus halting or slowing down the oxidative chain reaction process that leads to degradation. Primary antioxidants typically include, for instance, sterically hindered phenols, secondary aromatic amines, hydroquinones, p-phenylenediamines, quinolines, hydroxytriazines or ascorbic acid (vitamin C). Although aromatic amines are the strongest primary antioxidant, they are highly staining and seldom used in thermoplastics. Sterically hindered phenols are diverse in number as well as commercially available in high purity. Hindered phenols have been structurally classified as (1) alkylphenols, (2) alkylidinebisphenols, (3) thiobisphenols, (4) hydroxybenzyl compounds, (5) acylaminophenols, and (6) hydroxyphenyl propionates.

Secondary antioxidants are added to polymers mainly to provide needed short-term stability in melt flow and color during high temperature melt processing of the plastic material. They are believed to function by reacting with hydroperoxides to yield stable products that are less likely to fragment into radical species. Secondary antioxidants can usually be classified chemically as either a phosphorous-containing or a sulfur-containing compound. Phosphites such as triesters of phosphoric acid ($P(OR')_3$) are believed to react with hydroperoxides (ROOH) to form phosphates ($OP(OR')_3$) and alcohols (ROH). Elemental sulfur compounds and diaryl disulfides are reported to decompose hydroperoxides by generating sulfur dioxide. Thioethers ($R_1SR_2$) are believed to react with hydroperoxides (ROOH) to yield sulfoxides ($R_1SOR_2$) and alcohols (ROH). Sulfoxides may in turn destroy several equivalents of hydroperoxide through the intermediate formation of sulfenic acids and sulfur dioxide.

A third group of antioxidant stabilizers is commonly referred to as synergists. These materials may not be effective stabilizers when used alone, but when used in combination with another antioxidant a cooperative action results wherein the total effect is greater than the sum of the individual effects taken independently. Carbon black acts synergistically when combined with elemental sulfur, thiols or disulfides, whereas these materials are largely ineffective when used alone under the same conditions. Homosynergism is used to describe two stabilizers of unequal activity that work by the same mechanism. For example, two radical scavenging primary antioxidants might function synergistically if one were to transfer a hydrogen atom to the radical formed by the other, thus regenerating the latter stabilizer and extending its effectiveness. Alternatively, heterosynergism might result between a free radical scavenger and a nonradical hydroperoxide decomposer that act on different portions of the oxidative chain reaction process that leads to decomposition. Ultraviolet absorbers or metal deactivators in combination with radical scavengers have also been report to be heterosynergists. Some common thiosynergists include the esters of β-thiodipropionic acid, for example the lauryl, stearyl, myristyl or tridecyl esters. A widely used antioxidant package for polyolefins is the primary antioxidant 2,6-di-tert-butyl-4-methylphenol (BHT) with the thiosynergist dilauryl thiodipropionate (DLTDP), as both components of this combination are approved by the U.S. Food and Drug Administration for use in packaging materials for food products.

A conventional preferred antioxidant stabilizer combination known in the art to reduce discoloration in melt-processed polyolefins, and polypropylene in particular, includes a sterically hindered phenolic primary antioxidant with an organic phosphite or phosphonite secondary antioxidant. Bolton suggested using derivatives of phosphonic or phosphinic acids as stabilizers for polyolefins (U.S. Pat. No. 2,230, 371, German Pat. No. 1,210,855, and Belgian Pat. No. 617, 194) and Heinrich et al disclosed using diphosphonic and diphosphinic acid derivatives in combination with phenolic stabilizers in U.S. Pat. No. 4,024,103. More recently, the consensus view that a phenolic primary antioxidant with an organic phosphite or phosphonite secondary antioxidant is the preferred stabilizer combination to improve color and reduce melt flow instability during high temperature melt processing of polyolefins has been expressed many times, for instance, in U.S. Pat. No. 6,015,854, U.S. Pat. No. 6,022,946, U.S. Pat. No. 6,197,886, U.S. Pat. No. 6,770,693, and U.S. Pat. No. 6,881,744.

While combinations of antioxidant stabilizers are frequently employed in thermoplastic resins, often very specific combinations are optimized to address particular problems. Webster in U.S. Pat. No. 6,538,056 and U.S. Pat. No. 6,774, 170 discloses that polyethylene melt-phase compounded with oxidized, non-cationized, non-silylated sulfur black pigment, a phenolic antioxidant, a sulfur-containing secondary antioxidant (specifically the thiosynergist compound distearylthiodipropionate), and optionally containing carbon black or other inorganic fillers, exhibits improved long-term oxidative thermal stability in accelerated heating tests. Nakajima in JP10120833 disclose that the long-term thermal stability of a flame-retardant polyolefin comprising 30-70% by weight magnesium hydroxide, a polyol ester of a condensed aliphatic hydroxy acid, calcium stearate and a phenolic antioxidant, can be further improved by the addition of a thioether antioxidant. Oeysaed et al in WO2004033545 disclose that the long-term thermal stability of polypropylene is improved when a phosphite/phosphonite-type antioxidant is added along with a hindered phenol antioxidant and a sulfur-containing antioxidant (specifically the thiosynergist distearylthiodipropionate, IRGANOX PS-802) in accelerated heating tests. Inada et al in JP62270642 disclose improved adhesion to aluminum and stainless steel plates by polypropylene resin grafted with maleic acid and further containing calcium stearate, phenolic antioxidant (tetrakis[methylene-3-(3,5-di-t-butyl-4-hydroxyphenyl)propionate]methane, IRGANOX 1010) and dithioether antioxidant (distearyldisulfide, HOSTANOX SE-10).

A rapidly emerging application for silver based antimicrobial agents is inclusion in polymers used in plastics and synthetic fibers. A variety of methods is known in the art to render antimicrobial properties to a target fiber. The approach of embedding inorganic antimicrobial agents, such as zeolite, into low melting components of a conjugated fiber is described in U.S. Pat. No. 4,525,410 and U.S. Pat. No. 5,064, 599. In another approach, the antimicrobial agent may be delivered during the process of making a synthetic fiber such as those described in U.S. Pat. No. 5,180,402, U.S. Pat. No. 5,880,044, and U.S. Pat. No. 5,888,526, or via a melt extrusion process as described in U.S. Pat. No. 6,479,144 and U.S. Pat. No. 6,585,843. Alternatively, deposition of antimicrobial metals or metal-containing compounds onto a resin film or target fiber has also been described in U.S. Pat. No. 6,274,519 and U.S. Pat. No. 6,436,420. Still, the formation of colored species of silver that impart discoloration to a plastic composition or fiber is clearly undesirable from both an aesthetic and a practical materials performance perspective, and the prior art has not adequately addressed formation of thermoplastic polymer and silver compositions with desired color stability and low discoloration.

In addition to the color instabilities inherent to silver and to polymeric materials themselves, silver ion imbedded in polymer composites may react with polymer decomposition products (e.g. free radicals, peroxides, hydroperoxides, alcohols, hydrogen atoms and water), modifiers (e.g. chlorinated flame retardants), stabilizers and residual addenda (e.g. titanium tetrachloride, titanium trichloride, trialkylaluminum compounds and the like from Ziegler-Natta catalysts) to form potentially colored byproducts. This greater complexity of potential chemical interactions further challenges the modern worker in designing an effective stabilizer package for polymers containing silver species.

A number of approaches have been taken in the past to reduce discoloration resulting from the inclusion of silver-based compounds in melt-processed polymers. Niira et al in U.S. Pat. No. 4,938,955 disclose melt-processed antimicrobial resin compositions comprising a silver containing zeolite and a single stabilizer (discoloration inhibiting agent) selected from the group consisting of a hindered amine (CHIMASSORB 944LD or TINUVIN 622LD), a benzotriazole, a hydrazine, or a hindered phenol (specifically octadecyl 3-(3, 5-di-tert-butyl-4-hydroxyphenyl)propionate, commercially available as IRGANOX 1076). Reduction in long-term discoloration from exposure to 60 days of sunlight in the air was the only response reported.

Ohsumi et al in U.S. Pat. No. 5,405,644 disclose two fiber treatment processes in which the addition of a benzotriazole, preferably methylbenzotriazole, to treatment solutions subsequently inhibits discoloration in fibers comprising a silver containing tetravalent-metal phosphate antimicrobial agent. More specifically, addition of a benzotriazole to an ester spinning oil reduces discoloration in treated fibers following one day exposure to outdoor sunlight; and secondly, the addition of a benzotriazole to an alkali treatment solution reduces discoloration in treated fibers when examined immediately following treatment. It is suggested that the benzotriazole either retards the dissolution of silver ions or inhibits the reaction of small amounts of soluble silver ion with the various chemicals present in the fiber treatment solutions.

Lever in U.S. Pat. No. 6,187,456 discloses reduced yellowing of melt-processed polyolefins containing silver-based antimicrobial agents silver zirconium phosphate or silver zeolite when sodium stearate is replaced with aluminum magnesium hydrotalcite. Tomioka et al in JP08026921 disclose that discoloration from high temperature can be prevented for polypropylene compounded with a silver mixture containing specific amounts of sulfite and thiosulfate ion, if the antimicrobial silver mixture is impregnated on silica gel support. Dispersing silver-based antimicrobial agents into a wax or low molecular weight polymer as a carrier that is intern blended into a higher molecular weight polymer is disclosed in JP03271208A and JP2841115B2 as a safe means to handle higher concentrations of silver-based antimicrobial agents without staining the skin.

Some workers report reducing discoloration by simply combining silver-based antimicrobial agents with other antimicrobial agents in hopes of reducing the total amount of silver in a given formulation. Ota et al in JP04114038 combine silver sulfate with the organic antifungal agent TBZ (2-(4-thiazolyl)benzimidazole) to reduce discoloration in injection molded polypropylene. Herbst in U.S. Pat. No. 6,585,989 combines a silver containing zeolite and the organic antimicrobial agent TRICLOSAN® (2,4,4'-trichloro-2'-hydroxydiphenyl ether) in polyethylene and polypropylene to yield improved UV stabilization (less yellowness) in accelerated weathering tests. Kimura in U.S. Pat. No. 7,041,723 discloses that for polyolefins containing an antimicrobial combination consisting of (A) a silver containing zeolite and either (B) a silver ion-containing phosphate or (C) a soluble silver ion-containing glass powder, some drawbacks of each antimicrobial agent are mitigated, including the reduction of discoloration from UV light exposure in accelerated weathering tests.

There is a need to provide improved compositions comprising silver-based antimicrobial agents and thermoplastic polymers that substantially reduce the degree of unwanted discoloration within the resultant article due to the introduction of silver metal or silver ion salts.

SUMMARY OF THE INVENTION

In accordance with one embodiment, the present invention is directed towards a polymer composite comprising a thermoplastic polymer compounded with a phenolic antioxidant, an organo-disulfide antioxidant, and a silver-based antimicrobial agent. The specified combination of antioxidant stabilizers is superior in inhibiting undesirable discoloration of thermoplastic polymers in the presence of compounded silver-based antimicrobial agents. In a further embodiment, the invention is also directed towards a process of preparing such a composite, comprising compounding the phenolic antioxidant and organo-disulfide antioxidant with the thermoplastic polymer prior to compounding the silver-based antimicrobial agent with the thermoplastic polymer.

DESCRIPTION OF THE INVENTION

The object of the present invention is to provide improvements in color of melt-processed polymers and plastic objects made there of, within which a silver-based antimicrobial agent has been introduced. Polymers suitable to the invention include those melt-processed between about 130-300° C. Examples of such polymeric materials include:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked, known as PEX), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

2. Mixtures of the polymers mentioned above, for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Homopolymers and copolymers described above may have any stereostructure, including syndiotactic, isotactic, hemi-isotactic or atactic. Stereoblock polymers are also included. The polymers may be amorphous, crystalline, or semicrystalline; and possess a range of melt index, preferably from about 0.3 to about 99.

Polyolefins, i.e. the polymers of monoolefins exemplified in the preceding paragraphs, preferably polyethylene and polypropylene, can be prepared by different, and especially by the following, methods: a) radical polymerization (normally under high pressure and at elevated temperature); b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium (III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

Silver-based antimicrobial agents suitable for use in the invention are varied and may be classified as metallic silver, salts of silver ion, silver ion carriers or silver ion-exchange compounds, and silver containing glasses. Metallic silver is available in a number of physical forms, including coatings, microscopic filaments and particles of various shapes and sizes. Silver ion salts may be classified according to their aqueous solubility as highly, moderately or sparingly soluble. Examples of highly soluble silver salts are silver nitrate, acetate, citrate, chlorate, fluoride, perchlorate, propionate, etc. Some examples of moderately soluble silver ion salts are silver benzotriazole, borate, carbonate, lactate, sulfate, etc. Some examples of sparingly soluble silver ion salts are silver chloride, bromide, iodide, behenate, oxide and peroxide. Examples of silver ion carriers are the various forms of silver containing zeolite and silver deposited onto calcium phosphate or calcium silicate or silica gel. Silver ion-exchange compounds are exemplified by the silver zirconium phosphate type layered materials. Silver glasses include silicate, aluminosilicate and aluminozirconosilicate hosts that contain silver, for example. The choice of a silver-based antimicrobial agent is dependent on many factors given the particular polymer host and the end use of the composite. A preferred silver-based antimicrobial agent for incorporation into polyolefins is silver sulfate.

Silver sulfate employed in polymer composites of the present invention may be obtained from various commercially available sources (e.g., Riverside Chemical, Aldrich Chemical), and may be produced by conventional aqueous precipitation methods. The reaction of equimolar amounts of aqueous solutions of silver nitrate and sulfuric acid to form silver sulfate was described by Th. W. Richards and G. Jones, *Z. anorg. Allg. Chem.* 55, 72 (1907). A similar precipitation process using sodium sulfate as the source of sulfate ion was reported by O. Honigschmid and R. Sachtleben, *Z. anorg. Allg. Chem.* 195, 207 (1931). An alternate method employing the immersion of silver metal in a sulfuric acid solution was also reported by O. Honigschmid and R. Sachtleben (loc. cit.). Precipitation of finely divided silver sulfate from an aqueous solution via the addition of alcohol was later reported by H. Hahn and E. Gilbert, *Z. anorg. Allg. Chem.* 258, 91 (1949).

In accordance with a preferred embodiment, silver sulfate may be obtained by a process wherein an aqueous solution of a soluble silver salt and an aqueous solution of a source of inorganic sulfate ion are added together under turbulent mixing conditions in a precipitation reactor. Soluble silver salts that may be employed in the process include silver nitrate, acetate, propionate, chlorate, perchlorate, fluoride, lactate, etc. Inorganic sulfate ion sources include sulfuric acid, ammonium sulfate, alkali metal (lithium, sodium, potassium, rubidium, cesium) sulfate, and alkaline earth metal (such as magnesium) sulfate, transition metal (such as zinc, cadmium, zirconium, yttrium, copper, nickel, iron) sulfate, etc. In a specific embodiment, the soluble silver salt employed is silver nitrate and the source of inorganic sulfate ion is ammonium sulfate or sulfuric acid.

Turbulent mixing conditions employed in precipitation reactors may be obtained by means of conventional stirrers and impellers. In a specific embodiment, the reactants are contacted in a highly agitated zone of a precipitation reactor. Mixing apparatus, which may be used in accordance with such embodiment, includes rotary agitators of the type which have been previously disclosed for use in the photographic silver halide emulsion art for precipitating silver halide particles by reaction of simultaneously introduced silver and halide salt solution feed streams. Such rotary agitators may include, e.g., turbines, marine propellers, discs, and other mixing impellers known in the art (see, e.g., U.S. Pat. No. 3,415,650; U.S. Pat. No. 6,513,965, U.S. Pat. No. 6,422,736; U.S. Pat. No. 5,690,428, U.S. Pat. No. 5,334,359, U.S. Pat. No. 4,289,733; U.S. Pat. No. 5,096,690; U.S. Pat. No. 4,666, 669, EP 1156875, WO-0160511).

While the specific configurations of the rotary agitators which may be employed may vary significantly, they preferably will each employ at least one impeller having a surface and a diameter, which impeller is effective in creating a highly agitated zone in the vicinity of the agitator. The term "highly agitated zone" describes a zone in the close proximity of the agitator within which a significant fraction of the power provided for mixing is dissipated by the material flow. Typically, it is contained within a distance of one impeller diameter from a rotary impeller surface. Introduction of a reactant feed stream into a precipitation reactor in close proximity to a rotary mixer, such that the feed stream is introduced into a relatively highly agitated zone created by the action of the rotary agitator provides for accomplishing meso-, micro-, and macro-mixing of the feed stream components to practically useful degrees. Depending on the processing fluid properties and the dynamic time scales of transfer or transformation processes associated with the particular materials employed, the rotary agitator preferably employed may be selected to optimize meso-, micro-, and macro-mixing to varying practically useful degrees.

Mixing apparatus that may be employed in one particular embodiment includes mixing devices of the type disclosed in Research Disclosure, Vol. 382, February 1996, Item 38213. In such apparatus, means are provided for introducing feed streams from a remote source by conduits that terminate close to an adjacent inlet zone of the mixing device (less than one impeller diameter from the surface of the mixer impeller). To facilitate mixing of multiple feed streams, they may be introduced in opposing direction in the vicinity of the inlet zone of the mixing device. The mixing device is vertically disposed in a reaction vessel, and attached to the end of a shaft driven at high speed by a suitable means, such as a motor. The lower end of the rotating mixing device is spaced up from the bottom of the reaction vessel, but beneath the surface of the fluid contained within the vessel. Baffles, sufficient in number to inhibit horizontal rotation of the contents of the vessel, may be located around the mixing device. Such mixing devices are also schematically depicted in U.S. Pat. Nos. 5,549,879 and 6,048,683; the disclosures of which are incorporated by reference.

Mixing apparatus that may be employed in another embodiment includes mixers that facilitate separate control of feed stream dispersion (micromixing and mesomixing) and bulk circulation in the precipitation reactor (macromixing), such as descried in U.S. Pat. No. 6,422,736, the disclosure of which is incorporated by reference. Such apparatus comprises a vertically oriented draft tube, a bottom impeller positioned in the draft tube, and a top impeller positioned in the draft tube above the first impeller and spaced there from a distance sufficient for independent operation. The bottom impeller is preferably a flat blade turbine (FBT) and is used to efficiently disperse the feed streams, which are added at the bottom of the draft tube. The top impeller is preferably a pitched blade turbine (PBT) and is used to circulate the bulk fluid through the draft tube in an upward direction providing a narrow circulation time distribution through the reaction zone. Appropriate baffling may be used. The two impellers are placed at a distance such that independent operation is obtained. This independent operation and the simplicity of its geometry are features that make this mixer well suited in the scale-up of precipitation processes. Such apparatus provides intense micromixing, that is, it provides very high power dissipation in the region of feed stream introduction.

Once formed in an aqueous precipitation process, the resulting silver sulfate particles may be washed, dried and collected as a white free-flowing powder. In terms of particle size metrics, the precipitation process preferably results in producing both a small primary crystallite size and a small grain size, along with a narrow grain size distribution. While not limited in the present invention, average particle sizes of less than 100 micrometers, and even less than 50 micrometers, may be desired for particular product applications. Means of controlling the particle size of precipitated silver sulfate is disclosed in U.S. patent application Ser. No. 11/399, 754 filed Apr. 7, 2006, the disclosure of which is hereby incorporated by reference in its entirety.

In accordance with the invention, use of a combination of antioxidant stabilizers is employed to minimize discoloration of thermoplastic polymers due to compounding of silver-based antimicrobial agents therein. More particularly, the combination comprises a phenolic primary antioxidant and an organo-disulfide secondary antioxidant. When such a combination of antioxidant stabilizers is used along with a silver-based antimicrobial agent within a melt-process polymer composite, a surprising reduction in unwanted aesthetically displeasing discoloration is provided.

Phenolic antioxidants are typically stabilized by substitution at the positions adjacent to the hydroxy group in the phenol aromatic ring, and as such are commonly referred to as sterically hindered phenols or hindered phenols, and are well known to those of ordinary skill in the art. A non-limiting list of phenolic antioxidants suitable for use in the invention include:

2,6-di-tert-butyl-4-methylphenol (BHT)
2-tert-butyl-4,6-dimethylphenol
2,6-di-tert-butyl-4-ethylphenol
2,6-di-tert-butyl-4-n-butylphenol
2,6-di-tert-butyl-4-1-butylphenol
2,6-di-cyclopentyl-4-methylphenol 2-(α-methylcyclohexyl)-4,6-dimethylphenol
2,6-di-octadecyl-methylphenol
2,4,6-tri-cyclohexylphenol
2,6-di-tert-butyl-4-methoxymethylphenol
2,6-di-tert-butyl-4-methoxyphenol
2,5-di-tert-butyl-hydroquinone
2,5-di-tert-amyl-hydroquinone
2,6-diphenyl-4-octadecyloxyphenol
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
Esters of 3-(3,5-di-tert-butyl-4-hydroxyphenyl)-propionic acid or 3-(5-tert-butyl-4-hydroxy-3-methylphenyl)-propionic acid with monohydric or polyhydric alcohols, for example, methanol, octadecanol, 1,6-hexanediol, neopentyl glycol, thiodiethylene glycol, triethanolamine, diethylene glycol, triethylene glycol, pentaerythritol, tris-hydroxyethyl isocyanurate, di-hydroxyethyl oxalic acid diamide, triisopropanolamine.

Preferred phenolic antioxidants for use in the invention are the esters of 3-(3,5-di-tert-butyl-4-hydroxyphenyl)-propionic acid with monohydric or polyhydric alcohols described above. Most preferred is pentaerythrityl-tetrakis 3-(3,5-di-tert-butyl-4-hydroxy-phenyl)propionate (CAS No. 6683-19-8; CA Index Name: Benzenepropanoic acid, 3,5-bis(1,1-dimethylethyl))-4-hydroxy-,2,2-bis[[3-[3,5-bis(1,1-dimethylethyl)-4-hydroxyphenyl]-1-oxopropoxy]methyl]-1,3-propanediyl ester (9Cl); also commonly named tetrakis [methylene-3-(3,5-di-t-butyl-4-hydroxyphenyl)propionate] methane; commercially available as ANOX 20, CYANOX 2110, DOVERNOX 10, HOSTANOX O 10, IRAGNOX 1010)

Secondary antioxidants suitable as costabilizers along with the phenolic antioxidant are organo-disulfides. Organo-disulfides may be classified as diaryl, dialkyl or mixed alkylaryl disulfides. Specific embodiments include diphenyl disulfide and dioctadecyl disulfide (also named distearyl disulfide).

The basic procedures followed in producing the inventive stabilized antimicrobial plastic material or article comprise standard plastic formation techniques. Several basic methods exist of incorporating additives (such as silver-based antimicrobials and the inventive stabilizer combination, for example) within polymer articles on a large scale. One method is to dry blend a mixture of polymer, additives (e.g. modifiers and stabilizers), antimicrobials; melt the dry mix together in an extruder to form a molten composition which is then pelletized; and melting and subsequently molding such pellets into a plastic article. One preferred method is to dry blend a mixture of polymer and additives (e.g. modifiers and stabilizers), melt the dry mix together in an extruder to form a molten composition, followed by addition of the antimicrobial. Alternatively, one may mix conventional resin pellets and masterbatch concentrates containing the stabilizers and/or antimicrobial additives and molding in conventional molding equipment. Additional methods and preferred order of addition of additives, such as adding the antioxidant stabilizers of the invention prior to adding the silver-based antimicrobial agent, are described further below. The aforementioned molding steps may be performed preferably with injection molding equipment; however, other plastic-forming operations may also be utilized such as, and without limitation, blow molding, fiber extrusion, film formation, compression molding, rotational molding, and the like. These alternative plastic article-forming operations would be well understood and appreciated by one of ordinary skill in this art.

Besides the polymer, silver-based antimicrobial agents, and antioxidants, the composite material of the invention can include optional addenda. These addenda can include nucleating agents, antiblocking agents, basic co-stabilizers, blowing agents, fillers and reinforcing agents, plasticizers, light stabilizers and UV inhibitors, hindered amine stabilizers, metal inhibitors, surfactants, intercalates, lactones, compatibilizers, coupling agents, impact modifiers, chain extenders, colorants, dyes (such as ultramarine blue and cobalt violet), pigments (such as titanium oxide, zinc oxide, talc, calcium carbonate), lubricants, emulsifiers, antistatic agents, dispersants such as fatty amides (e.g., stearamide), metallic salts of fatty acids (e.g., zinc stearate, magnesium stearate), processing aids, additional antioxidants, synergists, fluorescent whiteners, fire retardants, abrasives or roughening agents such as diatomaceous earth, cross linking agents, foaming agents and the like. These optional addenda and their corresponding amounts can be chosen according to need. Incorporation of these optional addenda in the purge material can be accomplished by any known method.

Melt-processed polymers and plastics comprising a silver-based antimicrobial agent and the stabilizer combination of the invention to provide antimicrobial (antibacterial and/or antifungal) or antiviral protection without discoloration may be employed in a variety of applications. Typical end-use applications include, but are not limited to, extruded and non-extruded face fibers for area rugs (rugs with polypropylene face fibers (such as commercial, retail or residential carpet); carpet backing (either primary or secondary backing), or the latex adhesive backings used in carpet (commercial, residential or retail), or area rugs (commercial or residential)). In addition, melt-processed polymers of the invention may be used in liquid filtration media (such as non-woven filtration media for pools and spas, waste water treatment, potable water treatment, and industrial applications such as metalworking); non-woven air filtration media (such as commercial and residential furnace, HVAC or humidity control filters, air purifiers, and HEPA filters, and cabin air filters for automobiles and airplanes). Further, melt-processed polymers of the invention can be used for outdoor fabrics (such as woven and non-woven car and boat covers, tarps, tents, canvas, ducking, sails, ropes, pool covers, patio upholstery (such as umbrellas, awnings, seating), camping gear and geotextiles), building materials (such as drywall, weather stripping, insulation, housewrap and roof wrap, wall covering fabrics, flooring materials such as cement, concrete, mortar and tile, synthetic marble for kitchen and bath counters and sinks, sanitary ceramic composites, toilets, shower stalls and curtains, sealing materials (such as adhesives for plumbing and packaging, glazing for windows, tile and vitreous china, grout), push buttons for elevators, handrails for stairs, mats, and knobs), industrial equipment (such as tape, tubing, barrier fabrics, conveyor belts, insulators and insulation for wire and cable, plumbing supplies and fixtures, gaskets, collection and storage equipment (including piping systems, silos, tanks and processing vessels) and coatings used on the inside of fire system sprinkler pipes), daily necessities (such as chopping boards, disposable gloves, bowls, kitchen drain baskets, kitchen refuse baskets, kitchen knife handles, chopsticks, tableware, table cloths, napkins, trays, containers, bags, lunch boxes, chopstick cases, dusters, sponges, brooms, mops, wipes, bathroom stools, washbowls, pales, cupboards, soap cases, shampoo holders, toothbrush holders, toothbrushes, razor blade handles, wrapping films, food wraps and packaging, canteens, emergency water tanks, toilet seats, hairbrushes, brush bristles, combs, scrubbers, tools and tool handles, cosmetics and cosmetic containers, and clothing). Other uses envisioned include incorporation of the materials of the invention into stationary and writing materials (such as mechanical pencils, ball-point pens, pencils, erasers, floppy disk cases, clipboards, clear paper holders, fancy cases, video tape cases, photo-magnetic disk shells, compact disk cases, desk mats, binders, book covers, writing paper and pocket books), automobile parts (such as a steering wheels, armrests, panels, shift knobs, switches, keys, door knobs, assist grips, truck liners, convertible tops and interior liners), appliances (such as refrigerators, washing machines, vacuum cleaners and bags, air conditioners, clothing irons, humidifiers, dehumidifiers, water cleaners, dish washers and dryers, rice cookers, stationary and mobile telephones, copiers, touch panels for ATM or retail kiosks (e.g. photo-kiosks, etc.)), textile products (such as socks, pantyhose, undergarments, inner liners for jackets, aprons, gloves and helmets, towels, bathing suits, toilet covers, cushion pads, curtains, carpet fibers, fiberfill for quilts and pillows, pillows, sheets, blankets, bedclothes, bedding, mattress ticking, sleeping bags, mattress cover pads and filling, pillow covers, nose and mouth masks, towels, caps, hats, wigs, etc.) goods related to public transportation (such as overhead straps, handles and grips, levers, seats, seat belts, luggage and storage racks) sporting goods (such as balls, nets, pucks, whistles, mouth pieces, racket handles, performance clothing, protective gear, helmets, indoor and outdoor artificial turf, shoe linings and reinforcements, tools, structures and ceremonial objects used in athletic events and the martial arts), medical applications (such as bandages, gauze, catheters, artificial limbs, implants, instruments, scrubs, facemasks, shields, reusable and disposable diapers, sanitary napkins, tampons, condoms, uniforms, gowns and other hospital garments requiring aggressive and harsh cleaning treatments to allow the garment to be safely worn by more than one person). Miscellaneous applications for the invention further involve inclusion in musical instruments (such as in reeds, strings and mouthpieces), contact lens, lens keepers and holders, plastic credit/debit cards, sand-like materials for play boxes, jewelry and wrist watch bands.

Application of the materials of this invention in polymer-wood composites is also contemplated. With the rising cost of wood and the shortage of mature trees, there is a need to find good quality substitutes for wood that are more durable and longer-lasting (less susceptible to termite destruction and wood rot). Over the past several years, a growing market has emerged for the use of polymer-wood composites to replace traditional solid wood products in end-use applications such as extruded and foam-filled extruded building and construction materials (such as window frames, exterior cladding, exterior siding, door frames, ducting, roof shingles and related roofline products, and exterior boardwalks and walkways); interiors and internal finishes (for example, interior paneling, decorative profiles, office furniture, kitchen cabinets, shelving, worktops, blinds and shutters, skirting boards, and interior railings); automotive (including door and head liners, ducting, interior panels, dashboards, rear shelves, trunk floors, and spare tire covers); garden and outdoor products (such as decking, fence posts and fencing, rails and railings, garden furniture, sheds and shelters, park benches, playground equipment, and playground surfaces); and finally, industrial applications (including industrial flooring, railings, marine pilings, marine bulkheads, fishing nets, railroad ties, pallets, etc.). Polymer-wood composites also offer anti-sap-stain protection.

Polymer-wood composites may vary widely in composition, with polymer content typically ranging from about 3-80% by weight depending on end-use. Injection molded products require adequate flow of the molten material; and therefore, preferably contain from about 65 to 80% by weight of the polymer component. Whereas composites requiring structural strength may typically contain only about 3-20% polymer by weight, the polymer typically serving primarily as an adhesive. Perhaps the most commonly employed polymer components are the polyolefins (polyethylene or polypropylene, high density and low density versions and mixtures thereof), although polybutene, polystyrene, and other polymers with melting temperatures between about 130°-200° C. are also used. In principal, any polymer with a melt temperature below the decomposition temperature of the cellulosic fiber component may be employed. Crosslinking chemicals (such as peroxides and vinylsilanes), compatibilizers and coupling agents (such as grafted-maleic anhydride polymers or copolymers) that incorporate functionality capable of forming covalent bonds within or between the polymer and cellulosic components may be included. Cellulosic materials can be obtained from a wide variety of sources: wood and wood products, such as wood pulp fibers;

non-woody paper-making fibers from cotton; straws and grasses, such as rice and esparto; canes and reeds, such as bagasse; bamboos; stalks with bast fibers, such as jute, flax, kenaf, *cannabis*, linen and ramie; and leaf fibers, such as abaca and sisal; paper or polymer-coated paper including recycled paper and polymer-coated paper. One or more cellulosic materials can be used. More commonly, the cellulosic material used is from a wood source. Suitable wood sources include softwood sources such as pines, spruces, and firs, and hardwood sources such as oaks, maples, eucalyptuses, poplars, beeches, and aspens. The form of the cellulosic materials from wood sources can be sawdust, wood chips, wood flour, or the like. Still, microbes such as bacteria and fungus can feed on plasticizers or other additives and environmental foodstuffs found in or on the polymer component, resulting in discoloration and structural (chemical or mechanical) degradation. The present invention provides a means to more effectively address these issues by incorporating silver-based antimicrobial or antiviral agents in the polymer component of these composites without compromising the color of the final object.

Another emerging application to which the present invention is particularly applicable is antimicrobial nonwoven fabrics. In general, continuous filament nonwoven fabric formation involves supplying a low viscosity molten polymer that is then extruded under pressure through a large number of micro-orifices in a plate known as a spinneret or die, which creates a plurality of continuous polymeric filaments. The filaments are then quenched and drawn, and collected to form a nonwoven web. Microfilaments may typically be on the order of about 20 microns in diameter, while super microfilaments may be on the order of 3-5 microns. Continuous filament nonwoven fabrics formed from super microfilaments are mainly used in air filters, as well as in artificial leathers and wipes. Commercial processes are well known in the art for producing continuous microfilament nonwoven fabrics of polyethylene and polypropylene. The present invention enables production of melt-processed polypropylene comprising silver-based antimicrobial agents that may then be incorporated into such fine filaments with greatly reduced discoloration.

In accordance with the process of an embodiment of the present invention, a primary antioxidant and a secondary antioxidant of the invention can be combined with thermoplastic, including thermoset, polymers to form an initial composition, where the initial composition is defined as the antioxidants dispersed in polymer after thermal processing. After the initial composition is made, a composite of the invention is made, wherein the composite is defined as a silver-based antimicrobial agent such as silver sulfate, $Ag_2SO_4$, dispersed in the initial composition. Silver sulfate can be used as made, typically by a commercial precipitation process or by the precipitation process described below, or can be reduced in particle size using a mortar and pestle, ball mill, jet mill, attrition mill, and other techniques used for particle size reduction of solid particles.

A preferred method for making the composite of the silver-based antimicrobial agent, together with any optional addenda, in polymer is melt blending with the thermoplastic polymer using any suitable mixing device such as a single screw compounder, blender, paddle compounder such as a Brabender, spatula, press, extruder, or molder such as an injection molder. However, it is preferred to use a suitable batch mixer, continuous mixer or twin-screw compounder such as a PolyLab or Leistritz, to ensure proper mixing. Twin-screw extruders are built on a building block principle. Thus, mixing of the silver-based antimicrobial agent, temperature, mixing rotations per minute (rpm), residence time of resin, as well as point of addition of the silver-based antimicrobial agent can be easily changed by changing screw design, barrel design and processing parameters. Similar machines are also provided by other twin-screw compounder manufacturers like Werner and Pfleiderrer, Berstorff, and the like, which can be operated either in the co-rotating or the counter-rotating mode.

One method for making the initial composition is to melt polymer in a glass, metal or other suitable vessel, followed by addition of the antioxidants of the invention. The polymer and antioxidants are mixed using a spatula until the antioxidants are properly dispersed in the polymer, followed by the addition of a silver-based antimicrobial such as silver sulfate. The silver-based antimicrobial is mixed using a spatula until it is appropriately dispersed in the polymer. Another method for making the composite is to melt the polymer in a small compounder, such as a Brabender compounder, followed by addition of the antioxidants, compound until the antioxidants are properly dispersed in the polymer, followed by addition of the silver-based antimicrobial agent (e.g. silver sulfate) until it is appropriately dispersed in the polymer. Yet in another method such as in the case of a twin-screw compounder, this compounder is provided with main feeders through which polymer pellets or powders are fed. Antioxidants can be mixed with and fed simultaneously with the polymer pellets or powders. Antioxidants can also be fed using a feeder located downline from the polymer feeder. Both procedures will produce an initial composition. The silver-based antimicrobial agent (e.g. silver sulfate) is then fed using a top feeder or using a side stuffer. If the side stuffer is used to feed the silver-based antimicrobial agent then the feeder screw design needs to be appropriately configured. The preferred mode of addition of the silver-based antimicrobial material (e.g. silver sulfate) to the thermoplastic polymer is by the use of a side stuffer, although a top feeder can be used, to ensure proper viscous mixing and to ensure dispersion of the silver-based antimicrobial agent through the initial composition polymer matrix as well as to control the thermal history.

Alternatively, the initial composition containing the antioxidants of the invention can be compounded and collected, then fed through the main feeder before addition of the silver-based antimicrobial agent. In yet another embodiment, the silver-based antimicrobial agent can be pre-dispersed along with the antioxidants of the invention in the initial composition and compounded. The resulting composite material obtained after compounding can be further processed into pellets, granules, strands, ribbons, fibers, powder, films, plaques, foams and the like for subsequent use.

The weight ratio of antioxidants of the invention to thermoplastic polymer in the composite may vary widely depending on the type and amount of silver-based antimicrobial present and on the end-use of the polymer composite. However, it is preferred that the ratio is more than about 0.01:99.99, and less than about 2:8, more typically between 0.1:99.9 and 1:9. The resulting initial composition could be a masterbatch that can be further diluted in the compounder where the masterbatch is mixed with thermoplastic polymer.

The weight ratio of silver-based antimicrobial agent (e.g. silver sulfate) to thermoplastic polymer in the composite may vary widely depending on the end-use application. However, it is preferred that the ratio is at least 0.01:99.99, more preferably at least 0.05:99.95. The invention is particularly advantageous with respect to preventing undesired discoloration for polyolefin compositions comprising at least about 1 wt % silver sulfate. Preferably, the compositions need not contain more than about 10 wt % of silver-based antimicrobial agent to exhibit antimicrobial efficacy. The resulting composite could be a masterbatch that can be further diluted in a compounder where the masterbatch is mixed with thermoplastic polymer either simultaneously, same feeder, or sequentially, multiple feeders, resulting in a dilution of the masterbatch.

The following examples are intended to demonstrate, but not to limit, the invention.

EXAMPLES

Discoloration was visually appraised in the following examples in cases where the antioxidant combination of the invention was not present in melt-processed polyolefins containing a silver-based antimicrobial agent, as the intensity or darkness of the coloration was so great that these materials are greatly diminished in economic value. In these instances, the brown color approached that commonly seen in mud, dark leathers used in foot ware or baseball gloves, or in stained hardwoods used in furniture or flooring. Discoloration in stabilized materials was quantified by pressing a sample of the polymer composite into a flat plaque and measuring the spectral response in a HunterLab UltraScan XE colorimeter. Color is reported in terms of the 1976 CIE a* and b* coordinates, wherein a* is a measure of the redness or greenness of the plaque, and b* is a measure of the yellowness or blueness of the plaque. Values of a* and b* that are closer to zero represent less color and are indicative of superior inhibition of discoloration in polymer composites containing a silver-based antimicrobial. Preferred a* values have an absolute value less than 4.0, more preferably in the range of −1.5 to 4.0, even more preferred in the range −1.0 to 3.0, most preferred in the range −0.5 to 2.0. Preferred b* values have an absolute value less than 10.0, more preferably in the range −1.5 to 10.0, even more preferred in the range −1.0 to 8.0, and most preferred in the range −0.5 to 6.0. Further description of the colorimetric test procedure is contained in Billmeyer, F. W., et al., *Principles of Color Technology*, $2^{nd}$ Edition, pp. 62-64, published by John Wiley & Sons, Inc., 1981; or in ASTM Designations: D 2244-05 and D 1729-96.

Chemicals

The chemicals used in the following examples are:

| Product Name | Chemical Name | CAS No. | Supplier | Identifier |
|---|---|---|---|---|
| Polypropylene | | 9003-07-0 | Fibervision | PPFV |
| Polypropylene | | 9003-07-0 | Huntsman | PP049 |
| Polypropylene | | 9003-07-0 | Huntsman | PP022 |
| HOSTANOX O10 Primary Antioxidant | Pentaerythrityl-tetrakis 3-(3,5-di-tert-butyl-4-hydroxy-phenyl)propionate | 6683-19-8 | Clariant | O10 |
| HOSTANOX SE 10 Secondary Antioxidant Disulfide | Dioctadecyl disulfide | 2500-88-1 | Clariant | SE10 |
| HOSTANOX PAR 62 Secondary Antioxidant Phosphite | Bis(2,4-di-tert-butylphenyl) pentaerythritol diphosphite | 26741-53-7 | Clariant | PAR62 |
| IRGANOX 1081 Secondary Antioxidant Monosulfide | 6,6"-di-tert-butyl-2,2"-thiodo-p-cresol | 90-66-4 | Ciba Specialty Chemicals | 1081 |
| IRGANOX PS800 Secondary Antioxidant - Thiosynergist | Dilauryl-thiodipropionate | 123-28-4 | Ciba Specialty Chemicals | PS800 |
| SANDOSTAB P-EPQ Secondary Antioxidant Phosphonite | Tetrakis(2,4-di-tert-butylphenyl)4,4'-biphenylene diphosphonite | 119345-01-6 | Clariant | P-EQP |
| Diphenyl Disulfide Secondary Antioxidant Disulfide | | 882-33-7 | Eastman Kodak | DPDS |
| $Ag_2SO_4$ | Silver sulfate | 10294-26-5 | Riverside Chemical | XR |
| $Ag_2SO_4$ | Silver sulfate | 10294-26-5 | Preparation described below | X051 |
| $Ag_2SO_4$ | Silver sulfate | 10294-26-5 | Aldrich Chemical | XAL |

Preparation of Silver Sulfate Sample X051:

An eighteen-liter stainless steel sponge kettle was charged with 4 L of distilled water and the temperature controlled at 10° C. A planar mixing device (previously described in *Research Disclosure* 38213, February 1996 pp 111-114 "Mixer for Improved Control Over Reaction Environment") operating at 5000 rpm was used to ensure the homogeneity of the reactor contents. To this reactor 4.32 L of an 8M solution of $H_2SO_4$ was added. The resultant pH was <1. A peristaltic pump was used to deliver an 8 L solution containing 5.7M silver nitrate at a rate of 225 mL/min causing precipitation of a white product. The measured pH was <1. The reaction was held at 10° C. for 15 minutes. The final product was washed to a conductivity of <10 mS and dried at ambient temperature, followed by further drying for 2 hours at 150° C. Powder X-ray diffraction confirmed the product was compositionally homogeneous single-phase silver sulfate (designated sample X051).

Example 1—Comparative Check Sample

A Brabender paddle compounder was preheated to 200° C. and the mixing paddles were set to 60 rpm. Into the feed chamber was charged 40 grams of PPFV, and compounded 2 minutes under a dry nitrogen purge. The mixing paddles were stopped, and the feed chamber was dismantled. The compounded Example 1 sample was removed from the chamber walls and paddles, and pressed onto a stainless steel plate, with the original stainless steel plate temperature of 23° C. The pressed Example 1 sample was measured for color using a HunterLab UltraScan XE calorimeter, with a* and b* values recorded.

Example 2—Comparative Antioxidant

A Brabender paddle compounder was preheated to 200° C. and the mixing paddles were set to 60 rpm. Into the feed chamber was charged 39.8 grams of PPFV, and compounded 2 minutes under a dry nitrogen purge. Following the melting of the PPFV, 0.2 g of O10 was added to the feed chamber and the initial composition was compounded 1 minute under a dry nitrogen purge. The mixing paddles were stopped, and the feed chamber was dismantled. The compounded Example 2 sample was removed from the chamber walls and paddles, and pressed onto a stainless steel plate, with the original stainless steel plate temperature of 23° C. The pressed Example 2 sample was measured for color using a HunterLab UltraScan XE calorimeter, with a* and b* values recorded.

Example 3—Comparative Antioxidant

A Brabender paddle compounder was preheated to 200° C. and the mixing paddles were set to 60 rpm. Into the feed chamber was charged 39.8 grams of PPFV, and compounded 2 minutes under a dry nitrogen purge. Following the melting of the PPFV, 0.2 g of SE10 was added to the feed chamber and the initial composition was compounded 1 minute under a dry nitrogen purge. The mixing paddles were stopped, and the feed chamber was dismantled. The compounded Example 3 sample was removed from the chamber walls and paddles, and pressed onto a stainless steel plate, with the original stainless steel plate temperature of 23° C. The pressed Example 3 sample was measured for color using a HunterLab UltraScan XE calorimeter, with a* and b* values recorded.

Example 4—Comparative Antioxidant Combination

A Brabender paddle compounder was preheated to 200° C. and the mixing paddles were set to 60 rpm. Into the feed chamber was charged 39.6 grams of PPFV, and compounded 2 minutes under a dry nitrogen purge. Following the melting of the PPFV, 0.2 g of O10 and 0.2 g of SE10 was added to the feed chamber and the initial composition was compounded 1 minute under a dry nitrogen purge. The mixing paddles were stopped, and the feed chamber was dismantled. The compounded Example 4 sample was removed from the chamber walls and paddles, and pressed onto a stainless steel plate, with the original stainless steel plate temperature of 23° C. The pressed Example 4 sample was measured for color using a HunterLab UltraScan XE calorimeter, with a* and b* values recorded.

Example 5—Comparative Antioxidant Combination

A Brabender paddle compounder was preheated to 200° C. and the mixing paddles were set to 60 rpm. Into the feed chamber was charged 39.6 grams of PPFV, and compounded 2 minutes under a dry nitrogen purge. Following the melting of the PPFV, 0.2 g of O10 and 0.2 g of Par62 was added to the feed chamber and the initial composition was compounded 1 minute under a dry nitrogen purge. The mixing paddles were stopped, and the feed chamber was dismantled. The compounded Example 5 sample was removed from the chamber walls and paddles, and pressed onto a stainless steel plate, with the original stainless steel plate temperature of 23° C. The pressed Example 5 sample was measured for color using a HunterLab UltraScan XE calorimeter, with a* and b* values recorded.

Example 6—Comparative Antioxidant Combination

A Brabender paddle compounder was preheated to 200° C. and the mixing paddles were set to 60 rpm. Into the feed chamber was charged 39.6 grams of PP049, and compounded 2 minutes under a dry nitrogen purge. Following the melting of the PP049, 0.2 g of O10 and 0.2 g of 1081 was added to the feed chamber and the initial composition was compounded 1 minute under a dry nitrogen purge. The mixing paddles were stopped, and the feed chamber was dismantled. The compounded Example 6 sample was removed from the chamber walls and paddles, and pressed onto a stainless steel plate, with the original stainless steel plate temperature of 23° C. The pressed Example 6 sample was measured for color using a HunterLab UltraScan XE calorimeter, with a* and b* values recorded.

Example 7—Comparative Antioxidant Combination

A Brabender paddle compounder was preheated to 200° C. and the mixing paddles were set to 60 rpm. Into the feed chamber was charged 39.6 grams of PP049, and compounded 2 minutes under a dry nitrogen purge. Following the melting of the PP049, 0.2 g of O10 and 0.2 g of PS800 was added to the feed chamber and the initial composition was compounded 1 minute under a dry nitrogen purge. The mixing paddles were stopped, and the feed chamber was dismantled. The compounded Example 7 sample was removed from the chamber walls and paddles, and pressed onto a stainless steel plate, with the original stainless steel plate temperature of 23° C. The pressed Example 7 sample was measured for color using a HunterLab UltraScan XE calorimeter, with a* and b* values recorded.

Example 8—Comparative Combination

A Brabender paddle compounder was preheated to 200° C. and the mixing paddles were set to 60 rpm. Into the feed chamber was charged 38.0 grams of PPFV, and compounded 2 minutes under a dry nitrogen purge. Following the melting of the PPFV, 2.0 g of XR was added to the feed chamber and the composite was compounded 1 minute under a dry nitrogen purge. The mixing paddles were stopped, and the feed chamber was dismantled. The compounded Example 8 sample was removed from the chamber walls and paddles, and pressed onto a stainless steel plate, with the original stainless steel plate temperature of 23° C. The pressed Example 8 sample was measured for color using a HunterLab UltraScan XE calorimeter, with a* and b* values recorded.

Example 9—Comparative Antioxidant

A Brabender paddle compounder was preheated to 200° C. and the mixing paddles were set to 60 rpm. Into the feed chamber was charged 37.8 grams of PPFV, and compounded 2 minutes under a dry nitrogen purge. Following the melting of the PPFV, 0.2 g of O10 was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 9 sample was removed from the chamber walls and paddles, and pressed onto a stainless steel plate, with the original stainless steel plate temperature of 23° C. The pressed Example 9 sample was measured for color using a HunterLab UltraScan XE calorimeter, with a* and b* values recorded.

Example 10—Comparative Antioxidant

A Brabender paddle compounder was preheated to 200° C. and the mixing paddles were set to 60 rpm. Into the feed chamber was charged 37.8 grams of PPFV, and compounded 2 minutes under a dry nitrogen purge. Following the melting of the PPFV, 0.2 g of SE10 was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 10 sample was removed from the chamber walls and paddles, and pressed onto a stainless steel plate, with the original stainless steel plate temperature of 23° C. The pressed Example 10 sample was measured for color using a HunterLab UltraScan XE calorimeter, with a* and b* values recorded.

Example 11—Comparative Antioxidant

A Brabender paddle compounder was preheated to 200° C. and the mixing paddles were set to 60 rpm. Into the feed chamber was charged 37.8 grams of PP049, and compounded 2 minutes under a dry nitrogen purge. Following the melting of the PP049, 0.2 g of P-EPQ was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 11 sample was removed from the chamber walls and paddles, and pressed onto a stainless steel plate, with the original stainless steel plate temperature of 23° C. The pressed Example 11 sample was measured for color using a HunterLab UltraScan XE calorimeter, with a* and b* values recorded.

Example 12—Comparative Antioxidant Combination

A Brabender paddle compounder was preheated to 200° C. and the mixing paddles were set to 60 rpm. Into the feed chamber was charged 37.6 grams of PPFV, and compounded 2 minutes under a dry nitrogen purge. Following the melting of the PPFV, 0.2 g of O10 and 0.2 g of Par62 was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 12 sample was removed from the chamber walls and paddles, and pressed onto a stainless steel plate, with the original stainless steel plate temperature of 23° C. The pressed Example 12 sample was measured for color using a HunterLab UltraScan XE calorimeter, with a* and b* values recorded.

Example 13—Comparative Antioxidant Combination

A Brabender paddle compounder was preheated to 200° C. and the mixing paddles were set to 60 rpm. Into the feed chamber was charged 37.6 grams of PPFV, and compounded 2 minutes under a dry nitrogen purge. Following the melting of the PPFV, 0.2 g of O10 and 0.2 g of Par62 was added to the feed chamber and the initial composition was compounded 1 minute under a dry nitrogen purge. Following the compounding of the initial composition, 2.0 g of X051 was added to the feed chamber and the composite was compounded 1 minute under a nitrogen purge. The mixing paddles were stopped, and the feed chamber was dismantled. The compounded Example 13 sample was removed from the chamber walls and paddles, and pressed onto a stainless steel plate, with the original stainless steel plate temperature of 23° C. The pressed Example 13 sample was measured for color using a HunterLab UltraScan XE calorimeter, with a* and b* values recorded. Thus, similarly poor results to those in Example 12 were obtained using an alternate source of silver sulfate.

Example 14—Comparative Antioxidant Combination

A Brabender paddle compounder was preheated to 200° C. and the mixing paddles were set to 60 rpm. Into the feed chamber was charged 37.6 grams of PP049, and compounded 2 minutes under a dry nitrogen purge. Following the melting of the PP049, 0.2 g of O10 and 0.2 g of P-EPQ was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 14 sample was removed from the chamber walls and paddles, and pressed onto a stainless steel plate, with the original stainless steel plate temperature of 23° C. The pressed Example 14 sample was measured for color using a HunterLab UltraScan XE calorimeter, with a* and b* values recorded.

Example 15—Comparative Antioxidant Combination

A Brabender paddle compounder was preheated to 200° C. and the mixing paddles were set to 60 rpm. Into the feed chamber was charged 37.6 grams of PP049, and compounded 2 minutes under a dry nitrogen purge. Following the melting of the PP049, 0.2 g of O10 and 0.2 g of 1081 was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 15 sample was removed from the chamber walls and paddles, and pressed onto a stainless steel plate, with the original stainless steel plate temperature of 23° C. The pressed Example 15 sample was measured for color using a HunterLab UltraScan XE calorimeter, with a* and b* values recorded.

Example 16—Comparative Antioxidant Combination

A Brabender paddle compounder was preheated to 200° C. and the mixing paddles were set to 60 rpm. Into the feed chamber was charged 37.6 grams of PPFV, and compounded 2 minutes under a dry nitrogen purge. Following the melting of the PPFV, 0.2 g of O10 and 0.2 g of PS800 was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 16 sample was removed from the chamber walls and paddles, and pressed onto a stainless steel plate, with the original stainless steel plate temperature of 23° C. The pressed Example 16 sample was measured for color using a HunterLab UltraScan XE calorimeter, with a* and b* values recorded.

Example 17—Inventive Antioxidant Combination

A Brabender paddle compounder was preheated to 200° C. and the mixing paddles were set to 60 rpm. Into the feed chamber was charged 37.6 grams of PPFV, and compounded 2 minutes under a dry nitrogen purge. Following the melting of the PPFV, 0.2 g of O10 and 0.2 g of SE10 was added to the feed chamber and the initial composition was compounded 1 minute under a dry nitrogen purge. Following the compounding of the initial composition, 2.0 g of XR was added to the feed chamber and the composite was compounded 1 minute under a nitrogen purge. The mixing paddles were stopped, and the feed chamber was dismantled. The compounded Example 17 sample was removed from the chamber walls and paddles, and pressed onto a stainless steel plate, with the original stainless steel plate temperature of 23° C. The pressed Example 17 sample was measured for color using a HunterLab UltraScan XE calorimeter, with a* and b* values recorded.

Example 18—Inventive Antioxidant Combination

A Brabender paddle compounder was preheated to 200° C. and the mixing paddles were set to 60 rpm. Into the feed chamber was charged 37.6 grams of PPFV, and compounded 2 minutes under a dry nitrogen purge. Following the melting of the PPFV, 0.2 g of O10 and 0.2 g of SE10 was added to the feed chamber and the initial composition was compounded 1 minute under a dry nitrogen purge. Following the compounding of the initial composition, 2.0 g of X051 was added to the feed chamber and the composite was compounded 1 minute under a nitrogen purge. The mixing paddles were stopped, and the feed chamber was dismantled. The compounded Example 18 sample was removed from the chamber walls and paddles, and pressed onto a stainless steel plate, with the original stainless steel plate temperature of 23° C. The pressed Example 18 sample was measured for color using a HunterLab UltraScan XE calorimeter, with a* and b* values recorded. Thus, similarly improved results to those in Example 17 were obtained using an alternate source of silver sulfate.

Example 19—Inventive Antioxidant Combination

A Brabender paddle compounder was preheated to 200° C. and the mixing paddles were set to 60 rpm. Into the feed chamber was charged 37.6 grams of PPFV, and compounded 2 minutes under a dry nitrogen purge. Following the melting of the PPFV, 0.2 g of O10 and 0.2 g of DPDS was added to the feed chamber and the initial composition was compounded 1 minute under a dry nitrogen purge. Following the compounding of the initial composition, 2.0 g of X051 was added to the feed chamber and the composite was compounded 1 minute under a nitrogen purge. The mixing paddles were stopped, and the feed chamber was dismantled. The compounded Example 19 sample was removed from the chamber walls and paddles, and pressed onto a stainless steel plate, with the original stainless steel plate temperature of 23° C. The pressed Example 19 sample was measured for color using a HunterLab UltraScan XE calorimeter, with a* and b* values recorded. Thus, similarly improved color results to those in inventive Example 17 were obtained using a diaryl disulfide antioxidant instead of a dialkyl disulfide. However, the composite of Example 19 emitted a burnt rubber smell characteristic of thermally decomposed diphenyl disulfide.

Quantitative color measurements for Examples 1-19 are shown in Table 1 below:

TABLE 1

| Ex. | $Ag_2SO_4$ Source (5 wt %) | Primary Antioxidant (0.5 wt %) | Secondary Antioxidant (0.5 wt %) | a* | b* | Pass/Fail | Comment |
|---|---|---|---|---|---|---|---|
| 1 Comp. | — | — | — | −0.47 | 0.92 | Pass | pure PP check |
| 2 Comp. | — | HOSTANOX O10 | — | −1.29 | 2.39 | Pass | slightly discolored |
| 3 | — | — | HOSTANOX SE10 | −0.8 | 3.21 | Pass | slightly |

TABLE 1-continued

| Ex. | Ag$_2$SO$_4$ Source (5 wt %) | Primary Antioxidant (0.5 wt %) | Secondary Antioxidant (0.5 wt %) | a* | b* | Pass/Fail | Comment |
|---|---|---|---|---|---|---|---|
| Comp. 4 | — | HOSTANOX O10 | HOSTANOX SE10 organo-disulfide | 0.37 | 2.76 | Pass | slightly discolored |
| Comp. 5 | — | HOSTANOX O10 | PAR 62 phosphite | −0.85 | 0.48 | Pass | slightly discolored |
| Comp. 6 | — | HOSTANOX O10 | IRGANOX 1081 thiophenol | 0.03 | 2.98 | Pass | slightly discolored |
| Comp. 7 | — | HOSTANOX O10 | IRGANOX PS800 thiodipropionate | −1.23 | 1.78 | Pass | slightly discolored |
| Comp. 8 | X R | — | — | 4.01 | 14.96 | Fail | v. highly discolored |
| Comp. 9 | X R | HOSTANOX O10 | — | 1.04 | 12.56 | Fail | highly discolored |
| Comp. 10 | X R | — | HOSTANOX SE10 organo-disulfide | 1.12 | 11.15 | Fail | highly discolored |
| Comp. 11 | X R | — | SANDOSTAB P-EPQ phosphonite | 4.68 | 5.13 | Fail | highly discolored |
| Comp. 12 | X R | HOSTANOX O10 | PAR 62 phosphite | 5.16 | 20.71 | Fail | v. highly discolored |
| Comp. 13 | X 051 | HOSTANOX O10 | PAR 62 phosphite | 5.56 | 14.71 | Fail | highly discolored |
| Comp. 14 | X R | HOSTANOX O10 | SANDOSTAB P-EPQ phosphonite | 6.6 | 7.78 | Fail | highly discolored |
| Comp. 15 | X R | HOSTANOX O10 | IRGANOX 1081 thiophenol | 5.05 | 15.79 | Fail | v. highly discolored |
| Comp. 16 | X R | HOSTANOX O10 | IRGANOX PS800 thiodipropionate | 4.53 | 12.09 | Fail | v. highly discolored |
| Inv. 17 | X R | HOSTANOX O10 | HOSTANOX SE10 organo-disulfide | 1.29 | 5.98 | Pass | slightly discolored |
| Inv. 18 | X 051 | HOSTANOX O10 | HOSTANOX SE10 organo-disulfide | 1.47 | 5.70 | Pass | slightly discolored |
| Inv. 19 | X 051 | HOSTANOX O10 | Diphenyl Disulphide organo-disulfide | 0.97 | 5.93 | Pass | whiter, but smelly |

Comparisons among the results shown above in Table 1 for Examples 1-7 indicate that in the absence of a silver-based antimicrobial agent, addition of antioxidant stabilizers to polypropylene followed by melt-processing results in only slightly more discolored initial compositions. Comparison of Example 8 to Examples 1-7 illustrates that the discoloration impart by including a commercially available source of silver sulfate in melt-processed polypropylene is about an order of magnitude larger than that inherent in melt-processed polypropylene with or without antioxidants. Comparison of Examples 9-11 to Example 8 indicates that addition of any one antioxidant by itself (primary phenolic antioxidant (HOSTANOX O10) or secondary organo-disulfide (HOSTANOX SE10) antioxidant or the secondary phosphonite (SANDOSTAB P-EPQ) antioxidant) is, perhaps, at most marginally effective in reducing the discoloration of melt-processed polypropylene containing silver sulfate. Comparison of Examples 12-14 to Example 8 indicates that the addition of a combination of a primary phenolic antioxidant (HOSTANOX O10) and either a phosphite (HOSTANOX PAR 62) or phosphonite (SANDOSTAB P-EPQ) secondary antioxidant is not effective in substantially reducing the discoloration of melt-processed polypropylene containing silver sulfate. Comparison of Example 15 to Example 8 indicates that the addition of a combination of a primary phenolic antioxidant (HOSTANOX O10) and a thiophenol (IRGANOX 1081) secondary antioxidant is not effective in reducing the discoloration of melt-processed polypropylene containing silver sulfate. Comparison of Example 16 to Example 8 indicates that the addition of a combination of a primary phenolic antioxidant (HOSTANOX O10) and a thiodipropionate (IRGANOX PS800) thiosynergist antioxidant is not effective in reducing the discoloration of melt-processed polypropylene containing silver sulfate. Comparison of Examples 17-19 to Example 8 indicates that the addition of a combination of a primary phenolic antioxidant (HOSTANOX O10) and an organo-disulfide (IRGANOX SE10 or diphenyl disulfide) secondary antioxidant is very effective in reducing the discoloration of melt-processed polypropylene containing silver sulfate.

In summary, it has been discovered that the problem of discoloration associated with melt-processed polypropylene containing silver sulfate is about an order of magnitude larger than any discoloration due to thermal decomposition of the polymer itself. None of the antioxidants examined alone in this study were found to be effective. It has also been shown that the preferred antioxidant combinations known in the art for stabilizing melt-processed polyolefins, specifically the combination of a phenolic primary antioxidant and an organic phosphite or organic phosphonite secondary antioxidant, are ineffective in reducing the discoloration associated with melt-processed polypropylene containing silver sulfate. Likewise, the combinations of a phenolic primary antioxidant and either a thioether secondary antioxidant or thiosynergist (thiodipropionate (DLTDP)) are ineffective. Further, it has been discovered that the combination of a phenolic antioxidant (pentaerythrityl-tetrakis 3-(3,5-di-tert-butyl-4-hydroxy-phenyl) propionate) and an organo-disulfide antioxidant (e.g. dialkyl disulfide or diaryl disulfide) is surprisingly effective in reducing the discoloration associated with melt-processed polypropylene containing silver sulfate.

Example 20—Comparative Combination

Into a glass vessel was charged 20 grams of PP022. The vessel was then placed on a Corning hotplate set at heat setting 5. The polypropylene was heated until visually melted. One gram of XR was added to the melted polypropylene in the glass vessel. The composite was then stirred with a stainless steel spatula for 2 minutes. During this mixing step, the color of the composite turned brown. The resulting composite was removed from the glass vessel using the spatula and placed on a Teflon sheet and allowed to cool to room temperature (23° C.), giving a solid plaque. All mixing, melting and cooling steps occurred in ambient air. The color of the solid plaque was brown indicating that mixing of XR with polypropylene will not allow the generation of a low color silver sulfate-polypropylene composite. Thus, similarly poor results to those in Example 8 were obtained with an alternate commercial grade of polypropylene that is not stabilized with the antioxidant combination of the invention and for which a different compounding method was employed.

Example 21—Comparative Combination

Into a glass vessel was charged 21 grams of PP022. The vessel was then placed on a Corning hotplate set at heat setting 5. The polypropylene was heated until visually melted. One gram of XAL was added to the melted polypropylene in the glass vessel. The composite was then stirred with a stainless steel spatula for 2 minutes. During this mixing step, the color of the composite turned brown. The resulting composite was removed from the glass vessel using the spatula and placed on a Teflon sheet and allowed to cool to room temperature (23° C.), giving a solid plaque. All mixing, melting and cooling steps occurred in ambient air. The color of the solid plaque was brown indicating that mixing of XAL with polypropylene will not allow the generation of a low color silver sulfate-polypropylene composite. Thus, poor results similar to those in Example 8 were obtained with an alternate commercial source of silver sulfate, an alternate commercial grade of polypropylene, and a different compounding method.

Example 22—Comparative Combination

Into a plastic bag was charged 950 grams of PP022 and 50 grams of XR. The polypropylene pellets and silver sulfate powder of Example 22 were mixed in the plastic bag for 5 minutes, and then added to a mechanical feeder. The feeder was positioned to feed the Example 22 mixture into zone 1 of a PolyLab twin-screw compounder at a feed rate of 4 pounds per hour. The extruder barrel was preheated to 400° F., and the screw rpm was set at 400. All mixing, melting and cooling steps occurred in ambient air. The resulting composite was extruded as a strand and quenched to room temperature (22° C.) in a stationary water bath. The resulting solid strand from this noninventive example was brown indicating that mixing of XR with polypropylene will not allow the making of a low color silver sulfate-polypropylene composite. Thus, poor results similar to as those in Example 8 were obtained with an alternate commercial grade of polypropylene and a different compounding method.

Example 23—Inventive Antioxidant Combination

Into a plastic bag was charged 990 grams of PP022, 5 grams of O10, and 5 grams of SE10. The polypropylene pellets and antioxidant powders initial composition of Example 23 were mixed in the plastic bag for 5 minutes, and then added to a mechanical feeder. The feeder was positioned to feed the initial composition mixture into zone 1 of a PolyLab twin-screw compounder at a feed rate of 4 pounds per hour. The extruder barrel was preheated to 380° F., and the screw rpm was set at 400. All mixing, melting and cooling steps occurred in ambient air. The resulting initial composition was extruded as a strand and quenched to room temperature (22° C.) in a stationary water bath. The strand was cut into small pieces and dried at 70° C. for 30 minutes. The dried strands were fed into a polymer chopper generating small pellets. Into a plastic bag was charged 950 grams of initial composition pellets and 50 grams of XR. The initial composition pellets and silver sulfate powder of Example 23 were mixed in the plastic bag for 5 minutes, and then added to a mechanical feeder. The feeder was positioned to feed the initial composition and silver sulfate mixture into zone 1 of a PolyLab twin-screw compounder at a feed rate of 4 pounds per hour. The extruder barrel was preheated to 400° F., and the screw rpm was set at 400. All mixing, melting and cooling steps occurred in ambient air. The resulting composite was extruded as a strand and quenched to room temperature (22° C.) in a stationary water bath. The resulting solid strand from this inventive example was off-white indicating that mixing of this inventive composite of polypropylene, antioxidants including a disulfide secondary antioxidant, and commercially available silver sulfate will allow the making of a low color silver sulfate-polypropylene composite. Thus, improved results similar to those in Example 17 were obtained using a silver-based antimicrobial in combination with the antioxidants of the invention with an alternate commercial grade of polypropylene and a different compounding method.

The sample plaques were subsequently stored in dark conditions and the color of the polymer composites observed periodically over several months. No color changes were observed, indicating that the magnitude of the discoloration suffered by melt-processing polyolefins containing a silver-based antimicrobial agent greatly exceeds that due to long-term heat effects or melt-processing of the non-silver containing polymer itself.

In summary, the above Examples demonstrate that the beneficial results obtained for the inventive examples are independent of the commercial source of polypropylene, the source of silver sulfate, and can be realized by a number of compounding methods.

The invention claimed is:

1. A polymer composite comprising a thermoplastic polyolefin polymer compounded with a phenolic antioxidant, and organo-disulfide antioxidant, and antimicrobial agent comprising silver sulfate and wherein the composite has a colorimetric a* value greater than −0.5 and less 2.0 and a colorimetric b* value greater than −0.5 and less than 6.0.

2. The composite of claim 1, wherein the polyolefin comprises polypropylene.

3. The composite of claim 1, wherein the composite has an absolute colorimetric a* value less than 4.0 and an absolute b* value less than 10.0.

4. The composite of claim 1, wherein the composite comprises at least 1 wt % of silver sulfate.

5. The composite of claim 1, wherein the phenolic antioxidant is an ester of 3-(3,5-di-tert-butyl-4-hydroxyphenyl)-propionic acid with a monohydric of polyhydric alcohol.

6. The composite of claim 2, wherein the phenolic antioxidant is pentaerythrityl-tetrakis 3-(3,5-di-tert-butyl-4-hydroxy-phenyl)propionate.

7. The composite of claim 6, wherein the organo-disulfide is diphenyl disulfide or dioctadecyl disulfide.

8. The composite of claim 1, wherein the phenolic antioxidant is pentaerythrityl-tetrakis 3-(3,5-di-tert-butyl-4-hydroxy-phenyl) propionate and the organo-disulfide is diphenyl disulfide or dioctadecyl disulfide.

9. The composite of claim 8, wherein the polyolefin comprises polypropylene and the composite comprises at least 1 wt % of the silver sulfate, and has a colorimetric a* value greater than −0.5 and less 2.0 and a colorimetric b* value greater than −0.5 and less than 6.0.

10. The composite of claim 1, wherein the composite has a colorimetric a* value greater than −0.5 and less 2.0 and a colorimetric b* value greater than −0.5 and less than 6.0.

11. The composite of claim 1, wherein the phenolic antioxidant is an ester of 3-(3,5-di-tert-butyl-4-hydroxyphenyl)-propionic acid with a monohydric or polyhydric alcohol.

12. The composite of claim 1, wherein the organo-disulfide is diphenyl disulfide or dioctadecyl disulfide.

13. The composite of claim 1, wherein the phenolic antioxidant is pentaerytbrityl-tetrakis 3-(3,5-di-tert-butyl-4-hydroxy-phenyl)propionate and the organo-disulfide is diphenyl disulfide or dioctadecyl disulfide.

14. A process of preparing a polymer composite of claim 1, comprising a thermoplastic polyolefin polymer compounded with a phenolic antioxidant, and organo-disulfide antioxidant, and antimicrobial agent comprising silver sulfate, comprising hot melt compounding the phenolic antioxidant and organo-disulfide antioxidant with the thermoplastic polymer prior to compounding the silver-based silver sulfate antimicrobial agent with the thermoplastic polyolefin polymer, and wherein the polyolefin comprises polypropylene and the composite comprises at least 1 wt % of the silver sulfate, and has a colorimetric a* value greater than −0.5 and less 2.0 and a colorimetric b* value greater than −0.5 and less than 6.0.

15. The process according to claim 14, wherein the phenolic antioxidant is pentaerythrityl-tetrakis 3-(3,5-di-tert-butyl-4-hydroxy-phenyl)propionate and the organo-disulfide or dioctadecyl disulfide.

16. The process of claim 14 wherein the phenolic antioxidant is pentaerythrityl-tetrakis 3-(3,5-di-tert-butyl-4-hydroxy-phenyl)propionate and the organo-disulfide is diphenyl disulfide or dioctadecyl disulfide and the polyolefin polymer comprises polypropylene.

17. The polymer composite of claim 1 wherein the polymer composite has been formed by melt processing.

18. The polymer composite of claim 1 wherein the phenolic antioxidant, organic-disulfide and the polyolefin polymer are mixed together prior to adding the silver sulfate.

19. The polymer composite of claim 18 wherein the polymer composite has been formed by melt processing.

* * * * *